(12) United States Patent
Sadleir et al.

(10) Patent No.: US 9,763,579 B2
(45) Date of Patent: *Sep. 19, 2017

(54) INTERNAL BLEEDING DETECTION APPARATUS

(71) Applicant: E.I.T. PTY LTD., Kallaroo (AU)

(72) Inventors: Rosalind Sadleir, Tempe, AZ (US); Andrew Duncan, Mundaring (AU)

(73) Assignee: E.I.T. PTY, LTD, Kallaroo (AU)

( * ) Notice: Subject to any disclaimer, the term of this patent is extended or adjusted under 35 U.S.C. 154(b) by 581 days.

This patent is subject to a terminal disclaimer.

(21) Appl. No.: 14/279,358

(22) Filed: May 16, 2014

(65) Prior Publication Data

US 2014/0288404 A1    Sep. 25, 2014

Related U.S. Application Data

(62) Division of application No. 12/086,976, filed as application No. PCT/AU2006/001990 on Dec. 28, 2006, now Pat. No. 8,768,429.

(51) Int. Cl.
*A61B 5/02* (2006.01)
*A61B 5/00* (2006.01)
(Continued)

(52) U.S. Cl.
CPC ........ *A61B 5/02042* (2013.01); *A61B 5/0002* (2013.01); *A61B 5/053* (2013.01);
(Continued)

(58) Field of Classification Search
CPC ... A61B 5/02042; A61B 5/053; A61B 5/6831; A61B 5/0536; A61B 5/0002; A61B 5/0537; A61N 1/08
See application file for complete search history.

(56) References Cited

U.S. PATENT DOCUMENTS 4,617,939 A   10/1986   Brown et al.
4,763,660 A   8/1988   Kroll et al.
(Continued)

FOREIGN PATENT DOCUMENTS

JP   2002291912 A   10/2002
WO   2004021880 A   3/2004
(Continued)

OTHER PUBLICATIONS

Sadleir, Rosalind et al, "Detection Quantification of Intraperitoneal Fluid Using Electrical Impedance Tomography," IEEE Transactions on Biomedical Engineering, vol. 48, No. 4, Apr. 2001.
(Continued)

*Primary Examiner* — Rene Towa
(74) *Attorney, Agent, or Firm* — Geoffrey A. Lottenberg; Lewis Brisbois Bisgaard & Smith LLP

(57) ABSTRACT

An EIT system 1 adapted to detect internal bleeding in a body portion, the EIT system 1 comprising a plurality of electrodes 3 adapted in use to extend in a substantially linear orientation across one side only of the body portion and to be applied in electrical contact with the skin of the body portion, a current source adapted to cyclically apply an electric current between one pair of the electrodes 3, a voltage measuring means to measure the voltage across each of the other pairs of the electrodes resulting from the current, a data collection system 2 and a data analysis system 4 to analyze data resulting from the voltages that are measured by the voltage measuring means, wherein the analysis system 4 is configured to obtain quantitative information related to amounts and rates of conductive tissue changes occurring in the body, based on an EIT analysis equivalent to that obtained from data derived from electrodes spaced around the full perimeter of the body portion. Also disclosed is an
(Continued)

electrode belt suitable for bioelectrical use and in particular for detection of change of volume of tissue in a body portion.

11 Claims, 6 Drawing Sheets

(51) Int. Cl.
*A61B 5/053* (2006.01)
*A61N 1/08* (2006.01)

(52) U.S. Cl.
CPC .......... *A61B 5/0536* (2013.01); *A61B 5/0537* (2013.01); *A61B 5/6831* (2013.01); *A61N 1/08* (2013.01)

(56) References Cited

U.S. PATENT DOCUMENTS

| | | | |
|---|---|---|---|
| 6,236,886 B1 | 5/2001 | Cherepenin et al. | |
| 2004/0133123 A1* | 7/2004 | Leonhardt | A61B 5/026 600/547 |
| 2005/0020935 A1 | 1/2005 | Helzel et al. | |
| 2005/0215918 A1 | 9/2005 | Frantz et al. | |
| 2006/0058593 A1 | 3/2006 | Drinan et al. | |
| 2006/0260611 A1* | 11/2006 | Garber | A61B 5/0536 128/204.23 |

FOREIGN PATENT DOCUMENTS

| | | |
|---|---|---|
| WO | 2004036379 A | 4/2004 |
| WO | 2004082460 A | 9/2004 |

OTHER PUBLICATIONS

Sadleir, Rosalind et al., "Quantification of blood volume by electrical impedence tomography using a tissue-equivalent phantom," Phsiol. Meas., vol. 19, pp. 501-516 (1998).

* cited by examiner

INTERNAL BLEEDING DETECTION APPARATUS

FIELD OF THE INVENTION

The present invention relates to an apparatus and method for the analysis of body tissue by Electrical Impedance Tomography. It is particularly applicable for detecting or monitoring change in volume of the body tissue. A particular application of the invention is the detection of internal bleeding within a living body, particularly intraperitoneal bleeding. Also disclosed is an electrode belt suitable for bioelectrical use and in particular for detection of internal bleeding.

BACKGROUND ART

Electrical Impedance Tomography (EIT) is an imaging method that seeks to create cross-sectional maps of electrical resistivity or impedance distribution inside the body. This has previously been done using a 16 electrode array fixed to the external perimeter of a body about a transverse plane for example as described in U.S. Pat. No. 4,617,939 (Brown & Barber). The electrical current causes a change in the electrical potential on the surface of the body being examined. The other electrodes of the array are used to measure the electrical potential on the surface of the body and thereby monitor the electric field created by the current pattern. Distortions in the field pattern may be related to changes in the impedance distribution inside the body. As the solution of impedance distribution from surface voltage measurements is generally ill-posed, it has not been effective for producing good static images of body organs. This has limited the adoption of the technique for general use.

The EIT process may be contrasted with other bioelectrical procedures such as bioimpedance spectroscopy. Bioimpedance spectroscopy is a process whereby four electrodes are situated at standard reference points on the body (for example, right and left wrists, right and left ankles). The actual positioning of the electrodes could vary with application. The impedance measurements are made with this group of four. Two electrodes are nominated for current flow and the other two are used for measuring voltages. Impedance is measured as a function of frequency (say, over the range 1 kHz to 1 MHz) and the results may be displayed as an R vs. X (resistance vs. reactance) plot over this range or simply as the modulus |Z| or phase or some version of this. The impedance or R or X or related measure would be considered as a dependent variable of measures such as for example % water or % fat, sex, height, extent of bleeding (these being things that may be given a priori or solved for) in a standardized empirical function and so a given Z would be used to extract a parameter such as the extent of bleeding. The success of the process depends significantly on how good the empirical function is and how 'standard' the subject. Use of this procedure to detect intraperitoneal bleeding has had very limited success.

Serious injury to internal organs—for example, as can be suffered during blunt trauma associated with road accidents—is usually indicated by the presence of internal bleeding. It is the rate of the internal bleeding, in addition to the total amount of blood lost, which is indicative of serious injury and relative urgency of treatment. A rate of more than 30 ml per minute is usually an indication that intervention may be necessary. Bleeding is usually monitored by monitoring vital signs such as pulse rate, blood pressure and skin colour. However, this is not always a consistent way to detect serious internal bleeding—particularly among younger trauma victims.

The use of EIT for detecting bleeding was discussed in the paper: "Detection and Quantification of Intraperitoneal Fluid Using Electrical Impedance Tomography" by Rosalind J Sadleir and Richard A Fox, IEEE Transactions on Biomedical Engineering, Vol. 48, No. 4, April 2001, pages 484-491.

While EIT has shown considerable promise for detection of intraperitoneal bleeding and other uses, its use has been limited due to certain problems inherent in the technique as used to date. The problem solved by EIT is inherently non-linear which has limited the usefulness of images reconstructed according to linearized approximations. Additionally, the accuracy of the results is limited due to extraneous variations occurring during the test period. Chief amongst these is the effect of breathing. Impedance measurements are particularly sensitive to the changes in abdominal shape and lung air quantity during the breathing cycle. In addition, the electrodes previously used for obtaining EIT images of the abdomen have typically comprised a belt with 16 electrodes adapted to be positioned all around the perimeter of the abdomen. This can be problematic for practical use on patients, especially those where spinal injury is involved. Such belts have also been susceptible to pick up of electrical noise on voltage inputs.

Throughout this specification, the term "tissue" will be taken here to include fluids such as blood and lymphatic fluids as well as other types of tissue.

The above description of the prior art is given to assist the reader form an understanding of the nature of the invention disclosed herein. However, this description is not to be taken as indicating that the disclosure in that prior art in any way forms part of the common general knowledge in the art.

DISCLOSURE OF THE INVENTION

According to a first aspect, the invention resides in an EIT system adapted to detect changes in tissue volume within a body portion, the EIT system comprising a plurality of electrodes adapted in use to extend in a substantially linear orientation across one surface only of the body portion and to be applied in electrical contact with the skin of the body portion, a current source adapted to cyclically apply an electric current between one pair of the electrodes, a voltage measuring means to measure the voltage across each of the other pairs of the electrodes resulting from the current, a data collection system and a data analysis system to analyse data resulting from the voltages that are measured by the voltage measuring means, wherein the analysis system is configured to obtain quantitative information related to amounts and rates of conductive tissue changes occurring in the body, based on an EIT analysis equivalent to that obtained from data derived from electrodes spaced around the full perimeter of the body portion.

According to a preferred feature of the invention, the processing means establishes a model of the body portion under analysis comprising a plurality of elements and wherein a parameter representative of an electric field present in each element resulting from the current is calculated from the voltages that are measured and wherein the values of at least a portion of the parameters that are calculated for the elements are amended to substantially reconstruct values that would be obtained from measurements of voltages around the perimeter of the body portion and wherein the change of value of the parameter in a portion of elements over time is indicative of internal bleeding within the body portion.

According to a preferred feature of the invention, the data analysis system implements a series of steps to reconstruct the parameter values of the elements, the steps comprising:
calculate the difference between a reference data set and a measured data set of the voltages as measured to establish a vector;
multiply the data set by a reconstruction matrix to obtain a reconstructed image having a plurality of pixels;
integrate the values of the pixels in the reconstructed image to obtain a value of the parameter;
apply spatial filtering to correct for non-uniformity of parameter over the image plane
monitor change in the value of the parameter over a period of time to provide an indication of change of tissue volume.

According to a preferred feature of the invention, a detected change in tissue volume is representative of internal bleeding.

According to a preferred feature of the invention, the parameter is defined as Resistivity Index calculated in accordance with one of:

$$RI = \int_\Omega d\sigma\, dS \quad \text{or} \quad RI = \sum_{p=1}^{TP} d\sigma\, dA_p$$

for a two-dimensional array, or $$RI = \int_\Omega d\sigma\, dV \quad \text{or} \quad RI = \sum_{p=1}^{TP} d\sigma\, dV_p$$

for a three-dimensional array, where $dA_p$ and $dV_p$ are the areas or volumes of two or three dimensional image elements respectively.

According to a preferred feature of the invention, the data analysis system further implements the steps of:
using empirical sensitivity calibration to provide an estimate of the parameter in terms of blood volume;
dividing the estimated blood volume by time interval between reference and measured data sets to provide an estimate of the rate of bleeding;
determining an alarm category depending on the rate of bleeding that has been calculated:

According to a preferred feature of the invention, the data analysis system applies a digital filter to the data to provide temporal filtering of the data to thereby remove or at least minimise the effect of breathing on the EIT analysis.

According to a preferred feature of the invention, the electrodes are provided in a belt adapted to be lain across an anterior surface of the body portion and having a length such that the ends to not extend fully around said body portion, the electrodes being spaced along the length of the belt.

According to a preferred feature of the invention, each electrode comprises a contact face adapted to contact the skin of the body portion wherein the contact face is of elongate form having an elongate axis oriented substantially transverse to the linear spacing of the electrodes.

According to a preferred feature of the invention, the current source, voltage measuring means and data collection system are associated with an on-patient module adapted to be carried by the body having the body portion, wherein the data analysis system is provided by a remote processor and wherein data communication is provided between the on-patient module and the remote processor.

According to a preferred feature of the invention, the data communication is by wireless communication.

According to a preferred feature of the invention, the on-patient data module comprises processing circuitry and a telemetry transceiver that will allow data to be transferred to and from the processor.

According to a preferred feature of the invention, the processing circuitry selects the pair of electrodes to which a current is applied and the pair of electrodes across which voltage is measured at any point in time.

According to a further aspect, the invention resides in a method for detecting changes in tissue volume using an EIT system, the method comprising the steps of:
applying a current between a pair of electrodes spaced at the surface of a body portion;
measuring, at predetermined intervals, and at a multiplicity of locations in a plane through the body portion, the voltage between pairs of electrodes at the surface of the body portion resulting from the applied current to provide a set of voltage measurements, wherein the electrodes extend in a substantially linear orientation across one side only of the body portion;
determining the changes of the voltage measurement between consecutive sets of voltage measurements;
generating a reconstructed image of the body portion;
determining the resistivity index of the tissue within the body portion from the reconstructed image;
deriving a volume of tissue from the determined resistivity index;
determining the rate of change of tissue volume between consecutive sets of voltage measurements.

According to a preferred feature of the invention, the method includes the further step of initiating an alarm where the rate of change of tissue volume is above a predetermined value.

According to a preferred feature of the invention, the resistivity index is calculated by generating a vector indicative of the changes in voltage measurements between consecutive sets of voltage measurements; and multiplying the vector by a reconstruction matrix, the resultant matrix being the reconstructed image.

According to a preferred feature of the invention, the resistivity index is calculated by integrating the pixel values from the reconstructed image.

According to a further aspect the invention resides in an electrode belt adapted for use with an EIT system, the belt comprising a plurality of electrodes spaced along the elongate length of the belt and having contact faces adapted to make electrical connection with the skin of a body portion under examination wherein the belt is adapted to provide engagement of the electrodes on one side only of the body portion.

According to a preferred embodiment, the contact faces are substantially rectangular with a length in the range of 75 mm to 100 mm and a width in the range of 5 to 25 mm.

According to a preferred feature of the invention, the belt is flexible to enable the belt to conform to the profile of the body portion upon which it is placed to facilitate contact of each electrode with the body portion.

According to a preferred embodiment, the body portion is the abdomen and the ends of belt are formed with a curvature to facilitate contact of electrodes in the vicinity of the sides of the abdomen when in use.

According to a preferred embodiment at least some of the electrodes are provided with an adhesive surround to facilitate secure engagement of the electrode with the skin.

According to a further aspect the invention resides in an electrode belt adapted for use in bioelectrical measurements, wherein the belt is of elongate form having at least four electrodes spaced along the elongate length of the belt, the belt comprising a plurality of layers wherein the belt is constructed to provide active shielding.

According to a preferred feature of the invention, the belt comprises a core and shielding components, arranged in a multi-layer structure to provide active shielding.

According to a preferred feature of the invention, one of the outer layers comprises a plurality of apertures spaced along the length of the layers to thereby expose an underlying conducting layer and thereby define a corresponding plurality of electrodes.

According to a preferred feature of the invention, each electrode has a conductive track connecting each electrode with a termination.

According to a preferred feature of the invention, the belt is manufactured by a process similar to that used for printed circuit board manufacture.

According to a preferred feature of the invention, the belt is adapted for use with EIT measurements.

According to a further aspect, the invention resides an apparatus for detecting changes in tissue volume and its rate of change by EIT analysis comprising:
first processing means;
second processing means; and
electrode means adapted to apply a predetermined current between a pair of electrodes spaced at the surface of a body portion, under control of the first and second processing means and also adapted to measure in a plane through the body portion, the voltage between pairs of electrodes at the surface of the body portion resulting from the applied current to provide a set of voltage measurements, wherein the electrodes extend in a substantially linear orientation across one side only of the body portion;
the first processing means being operable to receive the set of measured voltages and to provide the set of voltage measurements to the second processing means, the first processing means being further operable to receive sets of voltage measurements at predetermined intervals and to provide these sets to the second processing means, the second processing means being operable to determine the changes in the voltage measurement between consecutive sets of voltage measurements; to provide a reconstructed image of the body portion; to determine the resistivity index of the tissue from the reconstructed image; to derive a volume of tissue from the determined resistivity index; and to determine the rate of change of tissue volume between consecutive sets of voltage measurements.

Preferably, the first processing means is further operable to measure voltage noise levels.

Preferably, the second processing means is further operable to initiate an alarm where the rate of change of tissue volume is above a predetermined value.

Preferably, the second processing means is operable to determine the resistivity index by calculating a vector indicative of changes in voltage measurements between consecutive sets of voltage measurements; multiplying the vector by a reconstruction matrix, the resultant matrix being the reconstructed image.

Preferably, the resistivity index is generated by integrating over pixels in the reconstructed image.

Preferably, the electrode means comprises a belt including a multiplicity of substantially equidistantly spaced electrodes, whereby current can be applied to any pair of the multiplicity of electrodes, and the voltage measured from one or more pairs of the multiplicity of electrodes.

Preferably, the first processing means is operable to apply current to all pairs of electrodes on the belt, and to take voltage measurements from all possible pairs of electrodes, for each current electrode pair.

Preferably, the second processing means is provided remote from the first processing means.

Preferably, the current is applied to all pairs of electrodes on the belt, and voltage measurements are measured from all possible pairs of electrodes, for each current electrode pair.

Thus, the apparatus and method of the present invention provides a significant number of advantages over known methods. It detects the rate of bleeding, and is particularly suitable for use with young people. It is non-invasive, low cost, and can avoid the need for surgery. It is small, portable and light and easy to use, and so could be used, for example, at the scene of an accident. In addition, it does not necessarily require special skills. It is sensitive, and can be used even for small amounts of fluid.

The belt has the advantage that it does need to be placed all the way around a patient's abdomen, thereby reducing any discomfort to the patient or risk of aggravating an existing injury, and facilitating its use for operators.

The invention will be more fully understood in the light of the following description of several specific embodiments:

BRIEF DESCRIPTION OF THE DRAWINGS

The description is made with reference to the accompanying drawings, of which.

DETAILED DESCRIPTION OF PREFERRED EMBODIMENTS

The embodiments of the invention are directed to an EIT system and method adapted to detect changes within a body. They are particularly suited to detecting internal bleeding within the peritoneum.

As previously mentioned, EIT systems apply a current to a body and measure voltage between electrodes placed on the surface of the body. From these measurements it has been possible to calculate the electric field which is created in a two-dimensional plane or three dimensional volume as a result of the electric current flow. A variation in electric field results from changes in resistivity of the various tissues within the region. From these resistivity changes, it is possible to create an image of changes in organs and tissue present in the region. While this has been done in the past, the quality of the images that have resulted have been quite poor and thus the process has had limited practical imaging application. The inventors have recognised that while intrinsic image quality may be poor, the process may be used to provide a parameter calculated from the output of an EIT imaging system which is subject to change and can be monitored in real-time. Internal bleeding is a particular phenomenon which causes the specified parameter to vary due to the significantly different resistivity of free blood in comparison with that of other tissue in the abdomen. Pooling of blood (or other conductive fluids) create a localised anomalous electrical conductivity which perturbs current flow within the body, and therefore perturb impedance measurements made on the body surface. These perturbations can be measured via the imaging process, to enable calculation of the rate of change, volume and location of the anomalous fluid. In this way the inventors have identified a manner in which EIT can be used to identify and monitor internal bleeding by non-invasive means.

As the most common cause of intraperitoneal bleeding is blunt trauma received in motor vehicle accidents the inventors have been concerned to develop apparatus that may be used for use with such patients who may well be suffering other injuries, including spinal injuries and/or be unconscious. EIT equipment of the prior art is often not suitable for use in such circumstances.

Figure 1:
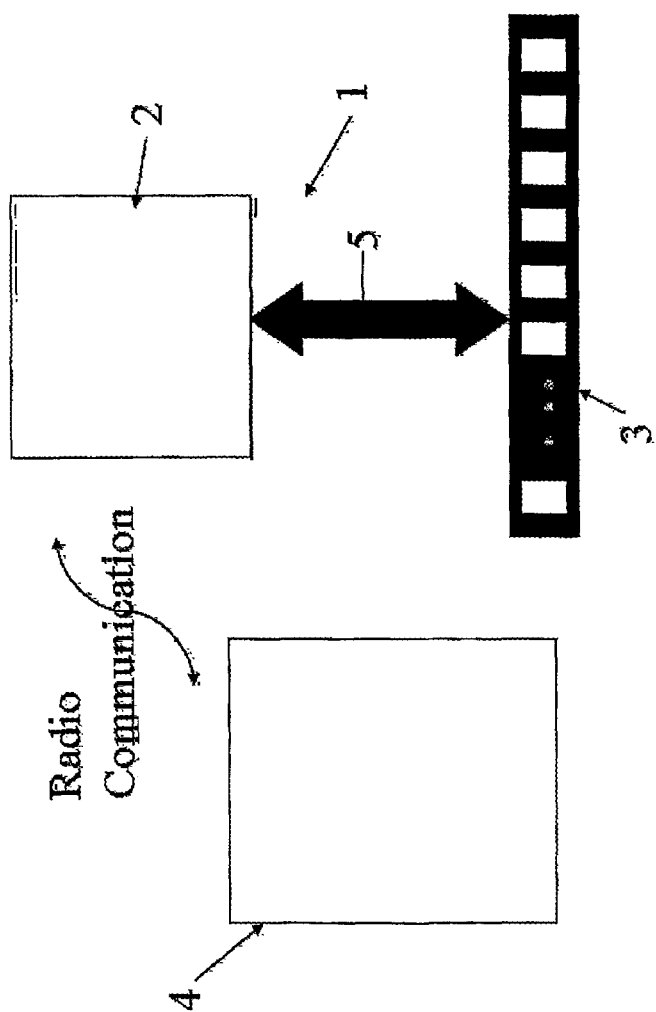
FIG. 1 is a block diagram of the component parts of the apparatus of the present invention.
Figure 2:
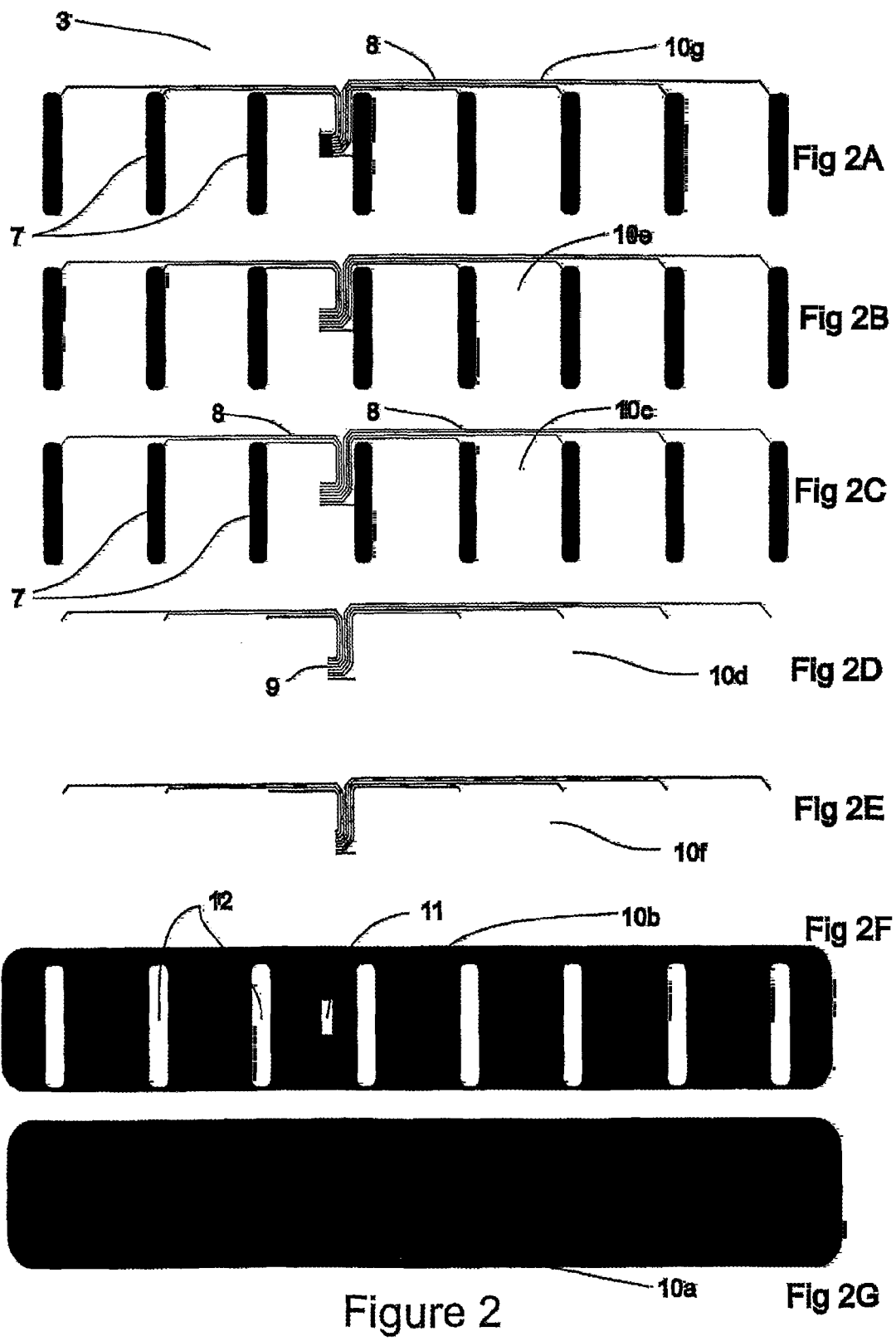
FIGS. 2A to 2G are plan views of the layers that make up the electrode belt of the apparatus of FIG. 1.
Figure 3:
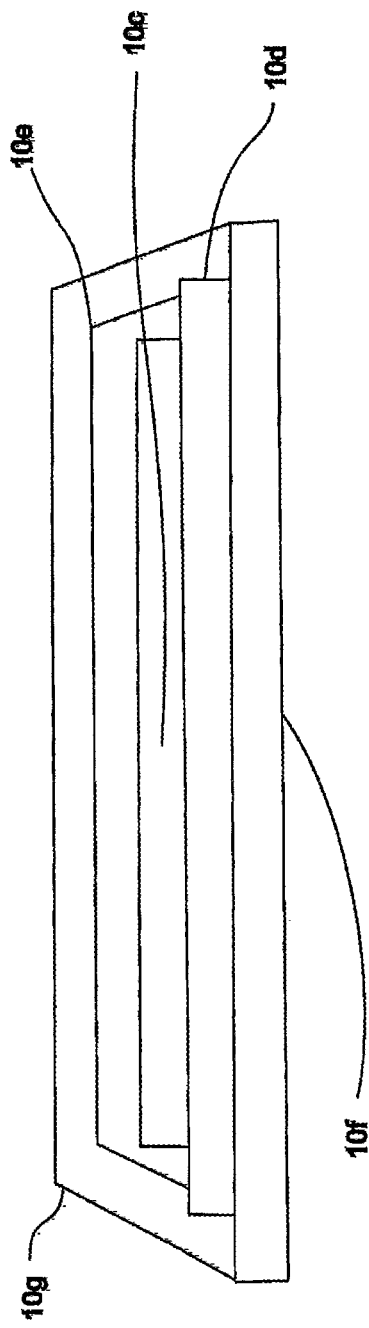
FIG. 3 is an enlarged schematic cross-section through an electrode on the belt of FIGS. 2A to 2G illustrating the layered structure.

The first embodiment is described with reference to FIGS. 1 to 6. As shown in FIG. 1, the first embodiment is an EIT system 1 adapted to detect internal bleeding in the peritoneum and comprises a flexible electrode belt 3, an on-patient module 2 and a processing means 4.

As better shown in FIGS. 2A to 2G, the electrode belt 3 is of elongate form having a plurality of electrodes 7 equally spaced along its length. Unlike the belts of the prior art which are adapted to be placed around the perimeter of the abdomen, the belt of the embodiment is arranged to be placed against the anterior surface of a patient's abdomen, so that it runs substantially from one side of the patient's abdomen to the other side. It is thus considerably shorter than conventional electrode belts which have been used for EIT. In typical use, the belt 3 is placed proximate the umbilicus. The belt has some flexibility to enable it to adapt to the contour of the abdomen and hold the contact faces of all electrodes in firm contact with the skin of the abdomen to thereby ensure satisfactory electrical conduction. In use, the contact faces are pre-gelled with an appropriate conductive paste to assist contact with the skin, and contact is further assured by means of adhesive surrounding each electrode face. It can be seen that the belt thus define a substantially linear array of electrodes across the abdomen, as required for EIT analysis. The electrode belt 3 is used to apply a current between a selected pair of the electrodes and to make measurements of voltages between remaining pairs of electrodes.

The contact faces of the electrodes are elongate and preferably of substantially rectangular form. The elongate axes of the contact faces are oriented transversely to the elongate direction of the belt, so that when the belt is applied to the abdomen the contact faces lie substantially parallel to a central axis of the abdomen. Elongate electrodes have been found to produce a more uniform parameter sensitivity in images. Internal bleeding can be present anywhere within a large region of the abdomen, and, in use, the belt 3 is usually applied centrally in the region of the umbilicus. The elongate shape of the contact faces of the electrodes ensures that the electric field applied to the abdomen is relatively uniform over a wide region of the abdomen and that, consequently, the rates estimated and gathered from the abdomen are relatively insensitive to their axial location relative to the electrodes. The length of the contact faces is selected as a compromise to provided extended length while ensuring good contact with the body. Typically, a length in the range of 75 mm to 100 mm has been found to be optimum, although lengths outside these limits will still function. The width is selected to ensure good contact area, while providing adequate spacing between electrodes. Typically, a width in the range of 5 mm to 25 mm has been found to be suitable.

The contact faces are composed of silver/silver chloride or any other suitable electrode material. Each electrode 7 has a conductive track 8 connecting the electrode 7 to an electrical termination 9.

While the EIT system of the invention can be adapted to function with electrode belts constructed in the manner of the prior art, it is very desirable to minimise electrical noise. Because the measurement of voltages between a pair of electrodes is intrinsically a high impedance measurement, when the voltage signals are processed, they are susceptible to noise. Thus, noise suppression or insulation must be used. In the present embodiment, active shielding is provided in which a coaxial configuration is used by means of the novel construction of the belt. In this way, signals are transmitted from the belt to the on-patient module 2, with the signal being applied both to the core and to the shield of the coaxial configuration. By doing this, there is no capacitive coupling between the shield and the core, because there is no differential voltage between the core and the shield. A low impedance shield voltage is generated using follower amplifiers in the on-patient module 2.

The electrode belt of the embodiment is constructed in a manner similar to a flexible printed circuit. In the present embodiment, the coaxial configuration is created using a seven-layer arrangement—as is illustrated in FIGS. 2A to 2G. FIGS. 2A to 2G each show one of the seven layers.

The two outer layers 10a, 10b comprise an insulating material and one 10a includes apertures 12 to allow the electrodes 7 to contact the patient's skin. There is also provided an aperture 11 for a termination 9.

As mentioned above, each electrode 7 comprises a core and shield arrangement. FIG. 2C illustrates the core layer 10c. The core layer comprises the electrodes 7, each electrode having a printed conductive strip 8, which will be used to connecting the electrode 7 to the coaxial cable 5. Each conductive strip 8 leads to a termination 9, which in turn connects to the coaxial cable 5. The conductive strips 8 are also made from a suitable conductive material such as silver. On either side of the core layer 10c are insulating layers 10d and 10e, which provide a layer of insulation between the core and the shielding. It can be seen from FIGS. 2A to 2G that one insulating layer 10e provides insulation over the electrodes 7, while the other layer 10d does not, thereby allowing the electrodes 7 to protrude through the apertures 12 on the outer layer 10b. On either outer side of the insulating layers 10d and 10e are the shielding layers 10f and 10g. These layers 10f, 10g include shielding for the electrodes 7 and conducting strips 8 of the core layer 10c, and are also made of a conductive material such as silver.

Figure 4:
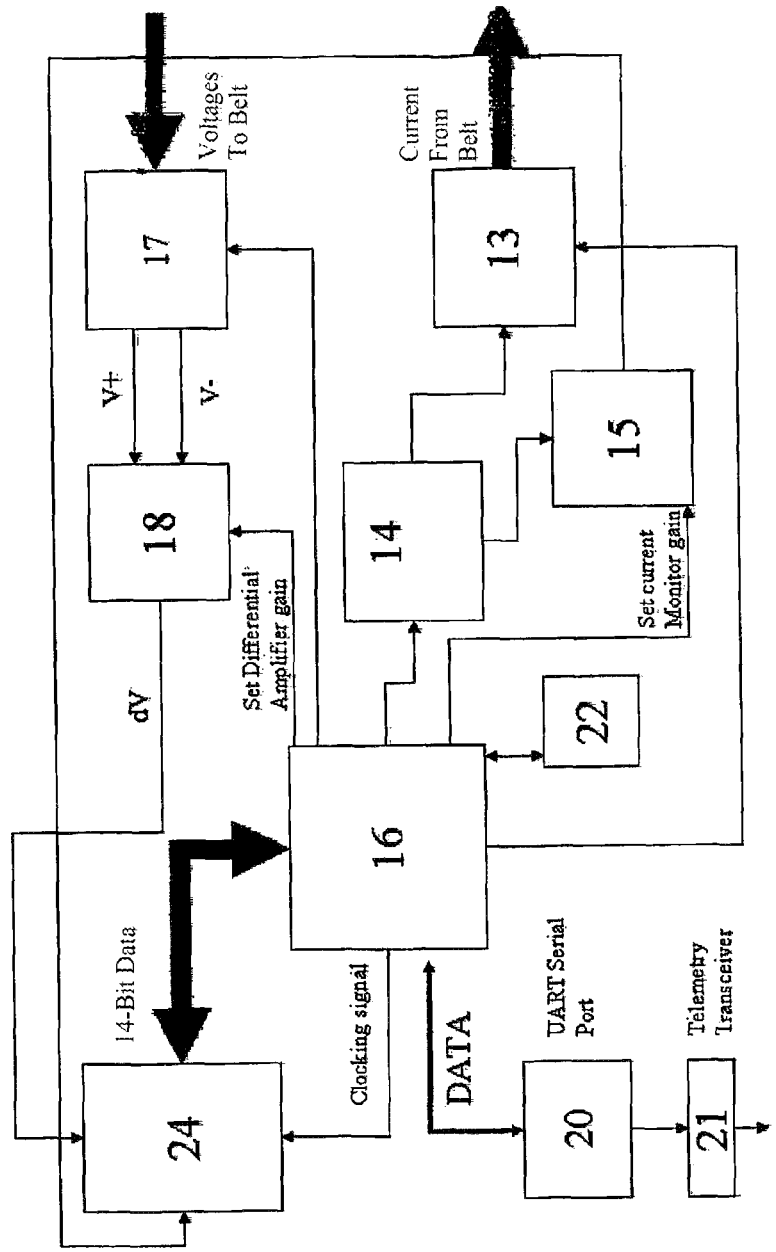
FIG. 4 is a schematic block diagram of the components of the on-patient module 2 of FIG. 1.

The two outer layers 10a, 10b are then placed on the outside. The belt 3 is printed using conventional printing techniques, with alternate layers of silver and insulating material. The traces of the different layers have different widths. The shielding layers 10f, 10g have the same, and thickest, width and are printed in silver. The insulating layers 10e, 10d have a smaller width and are printed in insulating material. The core layer 10c has the smallest width and is also printed in silver. If the shielding layer 10f is printed first, then subsequent layers laid down will take on the shape indicated in FIG. 4, thus forming a complete shielding layer around the core. FIG. 4 shows, as mentioned above, the detail of a single electrode 7, and illustrates this.

As mentioned above, the core and shielding conductive strips are terminated with a suitable termination 9 including a core portion and a shield portion that can then be coupled to a coaxial cable 5. The termination 9 comprises sixteen separate terminations—a core and shielding component for each electrode 7.

In this way, signals can be sent to and from the electrodes 7 from the on-patient module 2, to carry out the appropriate measurements as will be described in more detail below.

The on-patient module 2 comprises processing circuitry and a telemetry transceiver 21 that will allow data to be transferred to and from the processor 4. In the embodiment, the data is transmitted by wireless communication to remove the need for a physical connecting cable between the body under test and the processor. Nevertheless, it should be appreciated that a wired connection could be used as an alternative.

The components of the on-patient module 2 are illustrated schematically in FIG. 4. These components are standard components and are mounted, in a conventional, known manner on a printed circuit board (PCB) (not shown). The on-patient module 2 applies current to a selected pair of adjacent electrodes 7, and reads voltages from other pairs of adjacent electrodes 7. Current is supplied via a current multiplexer 13 and a constant current source in response to signals from a direct digital synthesiser (DDS) 14, and digital signal processor (DSP) 16. As an example, the DSP 16 can be an Analog Devices ADSP-2181 and the DDS 14 can be an Analog Devices AD9850. The actual current is provided by a current source 23 provided between the DDS 14 and the current multiplexer 13. A current monitor 15 measures the actual current applied to the electrodes 7—which may be slightly different to the constant current selected to be applied to the electrodes 7, due to the source resistance of the body—and transmits the measured value of the current to the DSP 16, to ensure that the correct current value of the current is communicated to the processor 4. The DDS 14 controls the frequency of the current signal to be applied to the current multiplexer 13. In the present invention, the current is usually selected at around 3 mA and 62 kHz, although this can be varied.

When current is applied to a pair of adjacent electrodes, then the resulting voltages between other pairs of electrodes on the electrode belt 3 are measured These voltages are input via a voltage multiplexer 17 to a differential amplifier 18 to provide a voltage difference, dV, which is then input to an analogue to digital converter (ADC) 24, which then provides a 14-bit data signal to the DSP 16 corresponding to this voltage difference.

Controlling signals and data can be sent to and from the DSP 16 to the remote processor 4 via a serial communications port 20. As mentioned above, this data is sent using radio telemetry, and a suitable radio telemetry transceiver 21 is provided on the on-patient module 2. However, it will be understood that other communications means—either wireless of fixed line—could be used. The on-patient module 2 also includes a battery (not shown), which supplies power to the components, as well as to the electrode belt 3.

The software for the on-patient module 2 resides on an EPROM 22. Upon reset of the DSP 16, it boots from the EPROM memory.

The software consists of a main routine and approximately 20 subroutines carrying out various functions. The main routine carries out the initialisation of the various circuit elements on the PCB and then enters an infinite loop waiting for events, to which it responds. Events are initiated by the receipt of characters on the serial port 20 of a UART board coupled to the DSP 16 and memory mapped into the DSP data area. The arrival of particular character strings causes selected activities to be executed within the software subroutines. Several interrupts are enabled for the DSP 16. A timer interrupt is used to start and stop activities that need to be done in a timely fashion. The transmission and reception of characters on the UART connected to the DSP is also done using interrupts.

Character strings sent to the UART 20 from the processor 4 are used to invoke the following activities:

Test whether the On-Patient Module 2 is on and communicating properly.

Select two electrodes on the electrode belt 3, to which the current is to be supplied.

Select electrodes on the electrode belt 3, from which voltages are to be measured—this is usually all other possible pairs of electrodes on the belt, that is apart from the electrodes to which the current is supplied.

Select the gain of the differential amplifier 18 used to amplify the voltage measured on the selected voltage electrodes.

Select the frequency for transmission of the signal to the electrodes i.e. that of the current applied to the belt 3. Four frequencies are available—15625 Hz, 31250 Hz, 62500 Hz and 125000 Hz. The default is 62500 Hz.

Carry out a single measurement of current (using the current monitor 15), and the voltage using the presently selected current and voltage electrode pairs from the belt electrodes 7.

Carry out a complete measurement of all possible voltage and current readings from all possible current electrode pairs on the electrode belt 3. In one instantiation, eight current source positions and forty voltage measurements are made in total. Electrode pairs include the two end electrodes between which measurements are taken/ current is applied.

Stop all measurements, calculations and activities being undertaken.

Measure On-Patient Module 12 battery health.

Prior to the initiation of the above functions—by the receipt of a character string by the UART serial port 20 connected to the DSP 16—the DSP 16 transmits a string back out the serial port 20 to the processor 4, to verify that the command was received. The DSP 16 carries out all the logic to convert the bit stream arriving at its serial port into meaningful characters. Characters sent through the UART serial port 20 are mapped into the memory of the DSP 16. The clocking signal of serial port 1 is used to control the triggering of the ADC 24. The timer interrupt is set up to allow timer interrupts to be used to start and stop data gathering. Interrupts for the reception and transmission of data on the serial port of the UART serial port 20 are enabled. All extraneous serial port interrupts are cleared and nesting of interrupts is disabled. Programmable flag pins are set to be outputs rather than inputs.

The DDS 14 operates in a conventional, known manner.

The current monitor 15 includes a programmable gain amplifier that amplifies the signal to the current monitor 15. The differential amplifier 19 amplifies either one of the battery signal or the voltage from the selected voltage electrodes. Both amplifiers have their gains set to one of 4 values. The gain of the current monitor PGA may be set to 1, 10, 100 or 1000. In practice it is set to 1000 because the current monitor signal is small. The gain of the other PGA is set to 1 (for battery signal) or 10, 100 or 1000 (for voltage measurement). Two control lines are required for both amplifiers to program one of the four gains. These control lines are connected to programmable flag outputs on the DSP 16 and thus gains are set by the DSP 16. A programmable switch is used to select what signals are sent to the second PGA above—that is either the voltages from electrodes 7 or battery voltage and subsequently to the ADC 24.

There are four 8-channel multiplexers on the PCB. Two are in the current multiplexer 13 and two are in the voltage multiplexer 17. The multiplexers select one of the eight electrodes 7 to be the positive current electrode, and a second to be the negative current electrode i.e. each selects one of the pair of electrodes to which the current is applied; and the positive voltage electrode and the negative voltage electrode i.e. the pair of electrodes between which a voltage measurement is taken. The multiplexers are set by logic levels supplied by two 8-output programmable latches connected to the DSP 16. One latch is programmed to output the four logic levels (3 inputs to set the channel and 1 to enable) required for each of the 2 multiplexers in the electrode current circuit and the other is likewise programmed to output settings for the voltage multiplexers. The latches reside on the data bus of the DSP 16 and are programmed with a write to the DSP's data bus.

A programmable switch is used to select whether the ADC 24 is supplied with a signal from the current monitor 15, or via the differential amplifier 18. This switch is set by a logic level output from a programmable flag on the DSP 16. Clocking of the ADC 24 is carried out by the clock line from serial port 1 on the DSP 16. No other use is made of serial port 1. Clocking of the ADC 24 is undertaken at a rate of 32 times the frequency transmitted through the current electrodes of the electrode belt 3. The clocking rate is set by writing a counter value into a register on the DSP 16.

The output of the ADC 24 is wired to the IDMA port on the DSP 16.

Prior to enabling a voltage or current measurement the IDMA port is set up to start writing into a particular memory location in the DSP's random access memory (RAM), thus storing the measured value at the selected memory location. The DSP's IDMA port increments the pointer to the write location after each analogue to digital conversion.

In one instantiation, 8000 samples of waveforms are recorded. This corresponds to 250 periods of the transmitted waveform with 32 measurements per period. The 14 bits from the ADC 24 are written into the 14 least significant bits of the chosen 16-bit location in the RAM. The second most significant bit is zero. The most significant bit is an overflow test bit from the ADC 24.

The 8000 samples are then used to provide a measured value for the current and voltage. Thus, after 250 periods are recorded for the required measurement, that measurement is processed and the results transmitted to the processor 4 via the UART serial port 20. A baseline level for each measurement is calculated. This is done to allow for voltage offsets on amplifiers, the ADC 24 and the electrodes 7.

In one instantiation, each of the 32 voltages in the period of the current or voltage waveform is estimated by averaging them over the 250 periods. This results in 32 numbers. Once appropriately normalised they are compared with the full averages over 250 periods to derive a standard deviation measure of the validity of signal measurement.

After subtraction of the baseline level, the amplitude of the AC signal from the current monitor or voltage electrodes is calculated by summing the square of the 32 averaged samples.

For calculation of the battery voltage (a DC signal), a simple normalised average of the 8000 samples is calculated.

Data and standard deviations are formatted as 32-bit real floating-point numbers and transmitted out the UART serial port 20 to the processor 4.

Figure 5:
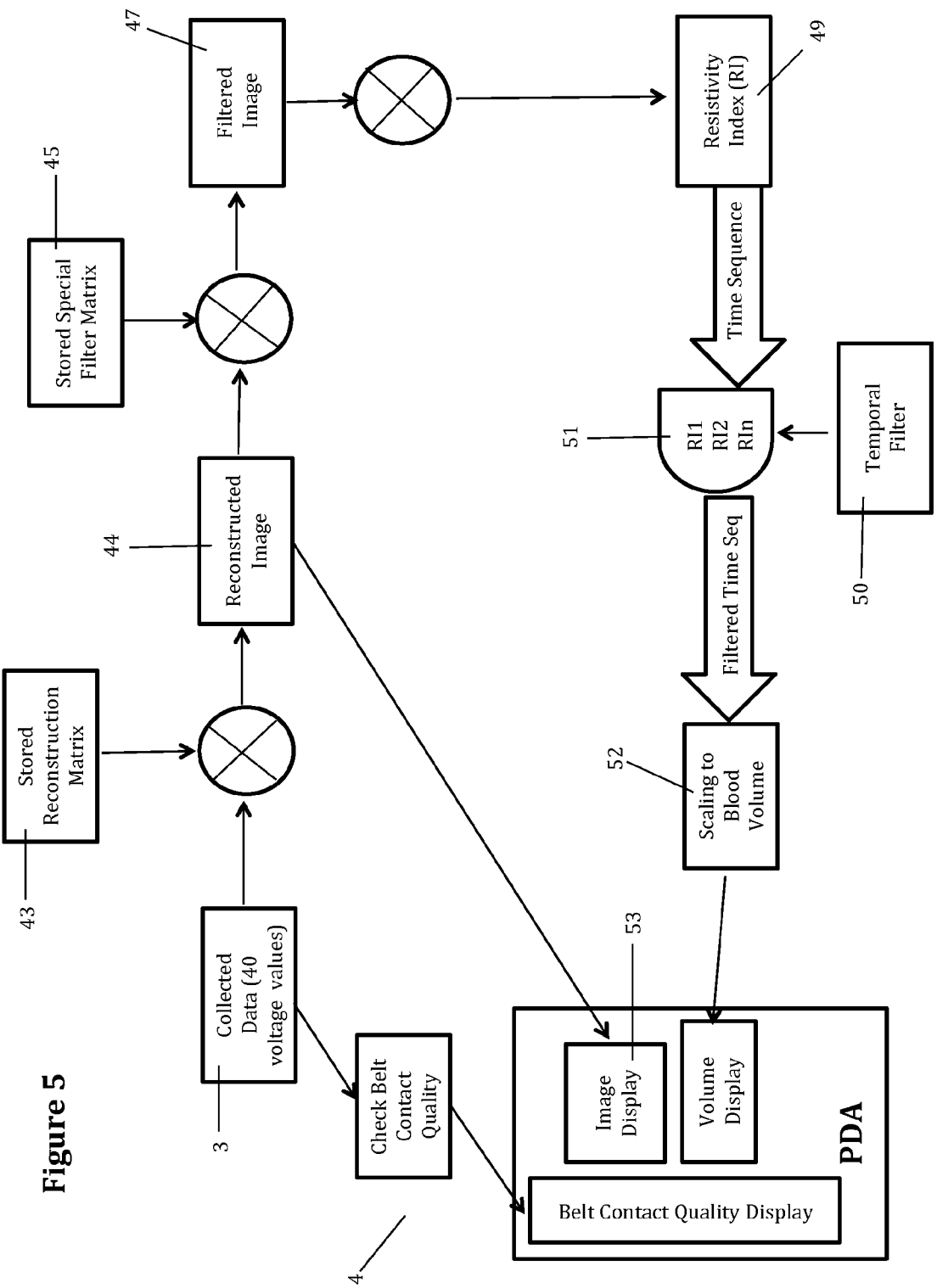
FIG. 5 is a diagrammatic representation of the processing flow of information by the processor.

The processing of the data by the processor 4 is represented diagrammatically by FIG. 5. The processor 4 may take any suitable form such as a handheld computer or personal digital assistant, for example a Hewlett Packard Jornada or iPAQ palm size computer or any serial capable device. In the embodiment, the processor is associated with a version of the Windows CE operating system, although it will be recognized that other suitable operating systems may be used.

The analysis of the data is directed to the calculation of a parameter which is representative of conductivity within the portion of the body being monitored. It is the change of this parameter which provides an indication in increase in volume of body tissue as in the case of internal bleeding. This parameter can be monitored over time to determine the rate of internal bleeding. This parameter has been termed the "Resistivity Index" (RI).

Figure 6:
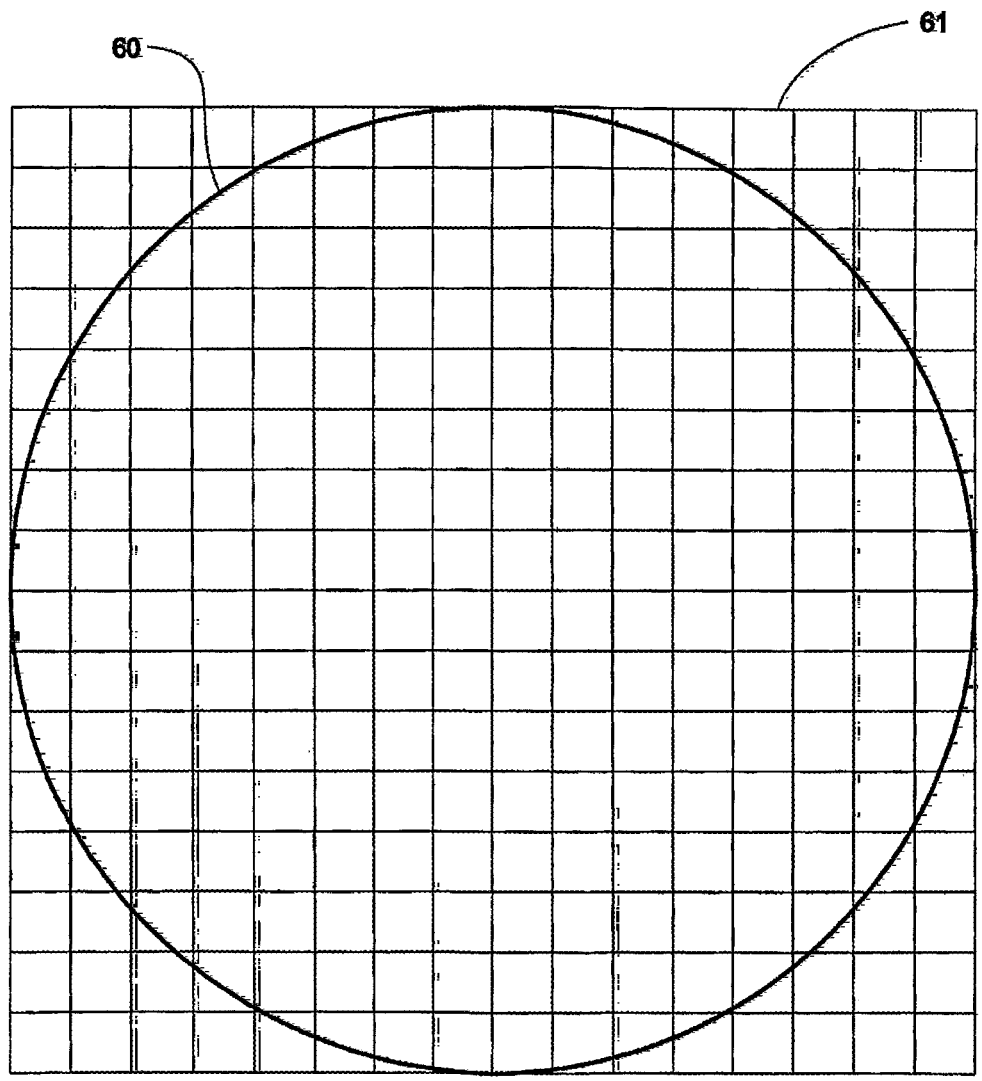
FIG. 6 illustrates a 16×16 array for use in representing data measured by the apparatus of FIG. 1.

In order to process the information, the abdomen may be modelled as a disk-shaped region. This is represented in FIG. 6. As shown in FIG. 6, the disk-shaped region 60 is represented by a 16×16 array 61. A 16×16 array is used on the basis that 16 electrodes would be placed substantially equidistantly around the circumference i.e. abdomen, with the applied electric field patterns resulting in values for electrical conductivity in the surrounding tissue at each of 256 array locations. This is typical of EIT processing that has been conducted in the prior art. However in principle there is no restriction on the number of pixels used in an image. The array may be represented as a planar surface in two dimensions as shown in FIG. 6, or may be mapped as a three dimensional cylindrical array of voxels.

The Resistivity Index involves adding up the total conductivity change observed within an image since this total change should reflect the total volume of anomaly that has appeared. In the case of the pixellation shown in FIG. 6, calculating the Resistivity Index will just involve adding all pixel values since all pixels are the same area, but in general should allow for variations in pixel size and therefore in general the Resistivity Index should be calculated by summing the quantity (dσdS) where S is the region described in the model, e.g. a cylinder.

The equation defining this relationship may thus be expressed as shown below for a two-dimensional array:

$$RI = \int_\Omega d\sigma \, dS$$

or for a three-dimensional array:

$$RI = \int_\Omega d\sigma \, dV$$

Alternatively, these may be expressed in discrete format. For a two-dimensional array, the relationship below is given, where $A_p$ is the area of the pixel in question and TP is the total number of pixels:

$$RI = \sum_{p=1}^{TP} d\sigma dA_p$$

For a three-dimensional array, the relationship below is given, where $V_p$ is the volume of the voxel in question and TP is the total number of voxels:

$$RI = \sum_{p=1}^{TP} d\sigma dV_p$$

As shown in FIG. 5, the processor 4 receives data from the on-patient module 2 which is operated on at 42 with the stored reconstruction matrix 43 to provide a reconstructed image 44. The image per se may be displayed on the display 53 of the processor. This image is then combined with stored spatial filter matrix 45 to provide a filtered image 47. A Resistivity index is then calculated at 49. Preferably, the Resistivity Index is processed with a temporal filter 50 at 51 to remove breathing effects. Finally a scaling is applied to derive a blood volume estimation. This process is now described in more detail below.

The processor 4 therefore receives information as to the voltages measured between respective electrode pairs for a given measured current between a predetermined pair of electrodes. Measurements are received for all possible electrode pairs. In an instantiation using 8 adjacent current electrode pair positions and adjacent voltage measurements this comprises a total of 40 measurements—that is for each electrode pair to which current is applied, there are 5 voltage measurements to be taken. There are 8 different electrode pairs (including the two end electrodes)—making the total number of measurements 40 i.e. 8×5. In addition, the actual current value measured between each of the eight adjacent current pairs is measured and transmitted, making a total of 48 measurements sent to the processor 4.

These 40 voltage measurements, normalised by dividing by each relevant current measurement, are saved to file in memory in the processor 4.

Routines concerned with data collection are:

| Routine Name | Function |
| --- | --- |
| select_measurement(int type); | Select Voltage, current or battery check |
| setup_current(int cPair); | Requests particular current pair be used |
| setup_shorted_current(int cPair); | Sets up shorted current source (used for measuring offsets in channels) |
| setup_volts(int vPair); | Requests particular voltage pair be used |
| get_data(double *mean, double *sigma); | Collect a particular data value |
| get_volt_data | |
| get_curr_data | |
| get_battery_data | |
| DataOnly(int nsamp); | Collect complete set of data without CSubject class |
| DataPresent( ); | Ping |

Other routines include:

| | |
| --- | --- |
| BatteryVoltsOK( ); | Entire routine to check on module battery voltage |

And routines concerned with Higher Level Data collection include:

| Routine Name | Function |
| --- | --- |
| CollectShortedData( ); | Collect a complete set of shorted data |
| CollectData(CSubject *patient); | Collect complete set of data |
| BreathingCycleOk(double *respIndex); | Function to filter out breathing cycle effects in measurements |
| Calibrate(BOOL *pflag, int *gflag, CSubject *patient, CVIndex *vValues); | Calibrate module |
| BeltContactOk(int contactNo); | Checks that RMS noise on differential voltage measurements is low. In this routine, for each adjacent voltage pair, the differential voltage is measured. If the standard deviation in the measurement is above a threshold, then it is determined that the contact of the belt to the patient is bad.) |

Processing these 40 measurements will give an indication of the conductivity of the tissue within the abdomen at the time that the measurement is taken. By repeating these measurements regularly at predetermined intervals, any changes in the measured conductivity indicates changes in the tissue composition e.g. through the presence of internal bleeding, as well as the approximate location of that change.

Once all the measurements have been saved to a file associated with the processor 4, then the processor 4 is operable to carry out the Reconstruct routine mentioned above, to determine the rate of change of blood volume in the abdominal cavity, and, if necessary, trigger any alarm.

Routines concerned with data reconstruction include:

| Routine Name | Function |
| --- | --- |
| LoadBMatrix(wchar_t *filename); | Reads in reconstruction matrix from file |
| void RemoveOffset(CCompleteMeas *data); | Removes offset from voltage and/or current data |

-continued

| Routine Name | Function |
|---|---|
| XferandNormalise(CSubject *mSubject, CCompleteMeas *set); | Normalises voltage data by current data, moves it to CSubject data structure |
| Process(Csubject *exp, Csubject *ref, Csubject *w); | Calculates vector of changes in data from reference set. This vector, denoted w, is multiplied by the reconstruction matrix to produce an image and hence an estimation of blood volume |
| Reconstruct(CSubject *ref, CSubject *exp, RIType *ri, RIType *riblood, BYTE *pixel, BOOL fStatus) | Process, reconstruct, estimate RI, embed image in larger background, interpolate |
| d_sparsemult(double *colinput, double *colresult, int n, int length, SPARSELIST *eltlist); | Performs multiplication of voltage differences by reconstruction matrix |
| Partial(Csubject *b, RIType *ri); | Sum Pixel Values |
| Discretize(double **bhires, int *pixels); | Rescale hiresolution image to 0->256 |
| Reconstruct(CSubject *w, CRecon *b) | Multiply Processed data by Reconstruction matrix |
| BloodConvert(RIType ri, RIType *riblood); | Convert Partial output (of RIType) to blood volume |
| CalculateRate(RIType *rate, RIType *blood); | Estimate rate in terms of blood quantity by dividing the quantity determined by output of Partial by time interval between this data and reference data collection time. |
| int CheckAlarm(RIType *rate); | Classify rate calculated below by severity |

In the present embodiment, eight electrodes are provided over half the abdomen—numbered "0" to "7"—and this must be accounted for, and which will be discussed further below.

By solving Laplace's equation for the region of interest (for the abdomen the region shape will usually be assumed cylindrical), the expected resultant electric field from current electrodes placed at positions around the circumference of the region 60 can be determined and can be used to derive expected conductivity values measured at any of the 256 locations within the array 61, for current electrode pairs placed around the circumference. Thus, a 256×256 reconstruction matrix can be derived from these calculations for all possible electrode pairs. This reconstruction matrix will be used by the processor 4 to provide indications of changes in tissue conductivity within the abdomen—as will be discussed in more detail below.

This Reconstruct routine comprises a number of sub routines.

A flow chart for this reconstruct routine is as follows:
1. Process—that is calculate the difference between reference (ref) and current (exp) data sets to obtain vector, w
   1.1. Reconstruct—this comprises multiplying the data vector w (256×1 matrix) by a reconstruction matrix (256×256) to obtain a reconstructed image.
2. If necessary, reduce spatial variation of image parameters by filtering, and apply temporal filtering to remove breathing artefacts
3. Integrate the pixels in (256×1 or 16×16) reconstructed image to obtain an RI estimate
4. Scale rate estimate using empirical sensitivity to obtain RI in terms of blood volume
5. Divide estimated blood volume by time interval between reference and current data sets
6. Depending on the rate that has been calculated, determine alarm category:

Thus, the process subroutine calculates the change between the present measurements and the last set of measurements—referred to herein as "exp" and "ref" respectively. Thus the change=(exp−ref). This is done by calculating a vector, w, of changes in data from the reference ("ref") data, which can later be multiplied by the reconstruction matrix to produce an image and hence an estimation of blood volume—as will be discussed in more detail below.

The resultant 256×1 matrix is an approximate reconstructed image, and, from there, values for the "resistivity index" (RI) can be obtained by integrating pixel values in this reconstructed image.

This RI value can then be used to provide an estimate of blood volume. This is done by using empirically derived values of blood volume as a function of RI. The value of estimated blood volume can be used to determine the rate of change of blood value by dividing the estimated blood volume by the time interval between the reference (ref) and current (exp) data sets, and if this value falls greater than a predetermined value, then an alarm can be triggered.

As mentioned above, variations to the measurements that can be attributed to the patient's breathing can be accounted for within the processing—if required.

The elongate shape of the electrodes 7, on the electrode belt 3, enable correlation between the reconstructed image and the amount of tissue that the image represents. Elongate electrodes overcome the problem that the use of conventional-shaped (small diameter, circular) electrodes would present, in that, if an amount of tissue such as blood, were to move a small axial distance out of the plane of the electrodes then the resistivity index would be very different. Providing elongate electrodes—as described above—overcomes this problem to some extent and allows the vector/reconstructed image to be used to derive the information required.

The processor can be used to select to a variety of parameters for operation and function. For example, the following functions are accessible using the processor 4:

Starts automatic collection at specified time intervals
Stop automatic measurements
Changes time interval between measurements
Checks RMS noise appearing on adjacent electrode voltage measurements to determine contact quality
Change the bleeding rate displayed between /sec, /min or /hr
Executes a measurement
Restarts measurements (change patient)
Saves data from a session
Checks for communication between the processor 4 and on-patient module 2
Setup communication (serial port) between the processor 4 and on-patient module 2
Checks Battery of module 2
Changes measurement frequency (at present measurements are made at 62.5 kHz).
Change phase of measurement e.g. to take quadrature (reactive) measurements rather than resistive measurements.

It will be obvious to person skilled in the art, that variations are possible within the scope of the present invention. For example, the apparatus could be used to detect other fluids or other tissue—such as cancerous tissue—and in other areas of the human body, and could be adapted for use with animals.

It will be appreciated that advances in technology may lead to other ways of implementing certain aspects of the embodiments. Those skilled in the art will appreciate that the wireless communication may be implemented in other ways than that described.

In an adaptation of the embodiment, the belt is provided with some stiffness to hold the belt in curved form, having greater curvature proximate the ends. Such a belt is adapted to support electrodes very close to the sides of patient, maintaining those electrodes in good contact with the skin. In the present embodiment mechanical contact between the skin and electrodes is facilitated by adhesive electrode surrounds.

It will be clear that the invention is not restricted to a belt having the number of electrodes described in the embodiment. With too few electrodes, there is insufficient resolution of voltage variations across the abdomen, so that is becomes impractical to generate a clear enough reconstruction using this method. For some uses, acceptable results may be obtained with a belt having only four electrodes, although for most uses, at least 8 electrodes would be preferred. The number of electrodes might also be increased above eight to improve resolution. Clearly, such an array will require more processing power and data transmission bandwidth to be effective. But the effectiveness of taking this step will be limited in any event. As the number of electrodes is increased, the relative resolution improvement reduces so that the benefit becomes insignificant.

It is also to be appreciated that the purpose of the belt is to provide a straightforward means of applying a group of electrodes to the skin in the desired area. It would also be possible provide a linear array of electrodes which are adapted to contact the skin in an arrangement which would not be considered as a belt in conventional terminology. For instance, the electrodes might be associated with a mattress such that contact with the electrodes might be maintained merely because the patient was to lie upon the mattress. Such an array would still contact the abdomen on one side only and require EIT analysis in the same manner as previously described to thereby provide the monitoring for internal bleeding.

Throughout the specification, unless the context requires otherwise, the word "comprise" or variations such as "comprises" or "comprising", will be understood to imply the inclusion of a stated integer or group of integers but not the exclusion of any other integer or group of integers.

We claim:

1. An EIT system adapted to detect changes in tissue volume in a body portion, the EIT system comprising
    a belt having a core layer, an insulating layer on either side of the core layer, a shielding layer on either side of each of the insulating layer, and an outer layer on either side of each the shielding layer, wherein the core layer comprises a plurality of spaced apart electrodes to be applied in electrical contact with skin of the body portion, wherein the insulating layers expose only one side of the electrodes, wherein each shielding layer comprises a conductive material providing circumferential shielding for the belt wherein one of the outer layers includes a plurality of apertures corresponding to said electrodes to provide engagement of only one side of the electrodes on the skin of the body portion:
    a current source adapted to cyclically apply an electric current between one pair of the electrodes,
    a voltage measuring means to measure the voltage across each of the other pairs of the electrodes resulting from the current,
    a data collection system and a data analysis system to analyse data resulting from the voltages that are measured by the voltage measuring means,
    wherein the analysis system is configured to obtain quantitative information related to amounts and rates of conductive tissue changes occurring in the body, based on an EIT analysis equivalent to that obtained from data derived from electrodes spaced around the full perimeter of the body portion.

2. An EIT system as claimed in claim 1 wherein the data analysis system establishes a model of the body portion under analysis comprising a plurality of elements and wherein a parameter representative of an electric field present in each element resulting from the current is calculated from the voltages that are measured and wherein the values of at least a portion of the parameters that are calculated for the elements are amended to substantially reconstruct values that would be obtained from measurements of voltages around the perimeter of the body portion and wherein the change of value of the parameter in a portion of elements over time is indicative of change in tissue volume within the body portion.

3. An EIT system as claimed in claim 2 wherein the data analysis system implements a series of steps to reconstruct the parameter values of the elements, the steps comprising:
    calculating the difference between a reference data set and a measured data set of the voltages as measured to establish a vector;
    multiplying the data set by a reconstruction matrix to obtain a reconstructed
image having a plurality of pixels;
    integrating the values of the pixels in the reconstructed image to obtain a value of the parameter; and
    monitoring change in the value of the parameter over a period of time to provide an indication of change in tissue volume.

4. An EIT system as claimed in claim 1 wherein a detected change in tissue volume is representative of internal bleeding.

5. An EIT system as claimed in claim 4 wherein the parameter is defined as Resistivity Index calculated in accordance with one of:

$$RI = \int_\Omega d\sigma\, dS \text{ or } RI = \sum_{p=1}^{TP} d\sigma\, dA_p$$

for a two-dimensional array, or $$RI = \int_\Omega d\sigma\, dV \text{ or } RI = \sum_{p=1}^{TP} d\sigma\, dV_p$$

for a three-dimensional array.

6. An EIT system as claimed in claim 5 wherein the data analysis system further implements the steps of:
using empirical sensitivity calibration to provide an estimate of the parameter in terms of blood volume;
dividing the estimated blood volume by time interval between reference and measured data sets to provide an estimate of the rate of bleeding;
applying a spatial filter to produce a resistivity index that is independent of bleeding location within imaged region
applying a temporal filter that reduces the effect on the resistivity index of shape and conductivity changes resulting from the subject's breathing cycle; and
determining an alarm category depending on the rate of bleeding that has been calculated.

7. An EIT system as in claim 1 wherein the data analysis system applies a digital filter to the data to provide temporal filtering of the data to thereby remove or at least minimise the effect of breathing on the EIT analysis.

8. An EIT system as in claim 1 wherein the current source, voltage measuring means and data collection system are associated with an on-patient module adapted to be carried by the body having the body portion, wherein the data analysis system is provided by a remote processor and wherein data communication is provided between the on-patient module and the remote processor.

9. An EIT system as claimed in claim 8 wherein the data communication is by wireless communication.

10. An EIT system as claimed in claim 8 wherein the on-patient data module comprises processing circuitry and a telemetry transceiver that will allow data to be transferred to and from the processor.

11. An EIT system as claimed in claim 10 wherein the processing circuitry selects the pair of electrodes to which a current is applied and the pair of electrodes across which voltage is measured at any point in time.

* * * * *